US010261026B2

(12) United States Patent
Urano et al.

(10) Patent No.: US 10,261,026 B2
(45) Date of Patent: Apr. 16, 2019

(54) DEFECT INSPECTION METHOD, LOW LIGHT DETECTING METHOD, AND LOW LIGHT DETECTOR

(71) Applicant: HITACHI HIGH-TECHNOLOGIES CORPORATION, Tokyo (JP)

(72) Inventors: Yuta Urano, Yokohama (JP); Toshifumi Honda, Yokohama (JP); Takahiro Jingu, Takasaki (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 211 days.

(21) Appl. No.: 15/398,911

(22) Filed: Jan. 5, 2017

(65) Prior Publication Data

US 2017/0115231 A1 Apr. 27, 2017

Related U.S. Application Data

(63) Continuation of application No. 13/882,542, filed as application No. PCT/JP2011/005752 on Oct. 14, 2011, now Pat. No. 9,588,054.

(30) Foreign Application Priority Data

Nov. 1, 2010 (JP) ................................ 2010-244915

(51) Int. Cl.
*G01N 21/88* (2006.01)
*G01N 21/95* (2006.01)
(Continued)

(52) U.S. Cl.
CPC ..... *G01N 21/8806* (2013.01); *G01N 21/4795* (2013.01); *G01N 21/8851* (2013.01);
(Continued)

(58) Field of Classification Search
USPC ....... 324/207.11, 97, 501; 250/205, 492, 23; 356/237.1, 237.5, 322, 323, 339, 340
See application file for complete search history.

(56) References Cited

U.S. PATENT DOCUMENTS 5,120,978 A 6/1992 Yamashita et al.
6,509,966 B2 1/2003 Ishiguro
(Continued)

FOREIGN PATENT DOCUMENTS

JP S63-055424 A 3/1988
JP 2-223845 A 9/1990
(Continued)

OTHER PUBLICATIONS

Office Action, dated Aug. 30, 2016, which issued during the prosecution of Japanese Application No. 2015-186274, which corresponds to the present application (English translation attached).
(Continued)

*Primary Examiner* — Vincent Q Nguyen
(74) *Attorney, Agent, or Firm* — Baker Botts L.L.P.

(57) ABSTRACT

A defect inspection method includes an illumination light adjustment step of adjusting light emitted from a light source, an illumination intensity distribution control step of forming light flux obtained in the illumination light adjustment step into desired illumination intensity distribution, a sample scanning step of displacing a sample in a direction substantially perpendicular to a longitudinal direction of the illumination intensity distribution, a scattered light detection step of counting the number of photons of scattered light emitted from plural small areas in an area irradiated with illumination light to produce plural scattered light detection signals corresponding to the plural small areas, a defect judgment step of processing the plural scattered light detection signals to judge presence of a defect, a defect dimension judgment step of judging dimensions of the defect in each
(Continued)

place in which the defect is judged to be present and a display step of displaying a position on sample surface and the dimensions of the defect in each place in which the defect is judged to be present.

1 Claim, 9 Drawing Sheets

(51) Int. Cl.
*G01N 21/956* (2006.01)
*G01N 21/47* (2006.01)

(52) U.S. Cl.
CPC ....... *G01N 21/9501* (2013.01); *G01N 21/956* (2013.01); *G01N 2021/8835* (2013.01)

(56) References Cited

U.S. PATENT DOCUMENTS

| | | |
|---|---|---|
| 6,710,879 B1 | 3/2004 | Hansen et al. |
| 2006/0215264 A1 | 9/2006 | Birk et al. |
| 2008/0304055 A1 | 12/2008 | Oshima et al. |
| 2009/0279081 A1 | 11/2009 | Urano et al. |
| 2009/0290168 A1 | 11/2009 | Hamamatsu et al. |
| 2010/0004875 A1 | 1/2010 | Urano et al. |

FOREIGN PATENT DOCUMENTS

| | | |
|---|---|---|
| JP | H02-223845 A | 9/1990 |
| JP | 8-304050 A | 11/1996 |
| JP | 2007-501934 A | 2/2007 |
| JP | 2008-268140 A | 11/2008 |
| JP | 2010-002406 A | 1/2010 |
| JP | 2010-14635 A | 1/2010 |
| WO | WO 2010/143367 A1 | 12/2010 |

OTHER PUBLICATIONS

Office Action, dated Mar. 13, 2015, which issued during the prosecution of Japanese Application No. 2014-121980, corresponds to the present application (Partial English translation attached).
Office Action in Korean Patent Application KR10-2013-7010821, dated May 22, 2014 (8 pgs., in Korean) [partial English language translation, 1 pg.].

DEFECT INSPECTION METHOD, LOW LIGHT DETECTING METHOD, AND LOW LIGHT DETECTOR

CROSS REFERENCE TO PRIOR APPLICATIONS

This application is a continuation of U.S. patent application Ser. No. 13/882,542, filed on Jul. 26, 2013, which is a U.S. National Phase application under 35 U.S.C. § 371 of International Application No. PCT/JP2011/005752, filed on Oct. 14, 2011, which claims benefit of priority to Japanese Application No. 2010-244915, filed on Nov. 1, 2010. The International Application was published in Japanese on May 10, 2012 as WO 2012/060057 A1 under PCT Article 21(2). The contents of the above applications are hereby incorporated by reference.

TECHNICAL FIELD

The present invention relates to a defect inspection method, a low light detecting method and a low light detector for inspecting a minute defect existing on the surface of a sample and judging a position, a kind and dimensions of the defect to be outputted.

BACKGROUND ART

In a manufacturing line of semiconductor substrates, thin-film substrates and the like, in order to maintain and improve the yield of products, inspection of a defect existing on the surface of the semiconductor substrates, the thin-film substrates and the like is performed. As prior arts of the defect inspection, JP-A-8-304050 (Patent Literature 1), JP-A-2008-268140 (Patent Literature 2) and the like are known.

The Patent Literature 1 describes that "the same defect is illuminated plural time in one inspection by an illumination optical system which makes linear illumination and a detection optical system which divides an area to be illuminated by a line sensor and detects a defect and scattered light therefrom is added to thereby improve the detection sensitivity".

The Patent Literature 2 describes that "2n APD's corresponding to laser light bands are arranged linearly" and "proper pairs of the 2n APD's are combined to calculate differences in output signals of the combined paired APD's, so that noise due to reflected light is erased and defect pulse for scattered light is outputted".

CITATION LIST

Patent Literature

Patent Literature 1: JP-A-8-304050
Patent Literature 2: JP-A-2008-268140

SUMMARY OF INVENTION

Technical Problem

The defect inspection used in the manufacturing process of semiconductors and the like demands detection of a minute defect, high-accuracy measurement of dimensions of the detected defect, inspection of a sample without destruction (for example, without changing the sample in quality), acquisition of substantially fixed inspection results in terms of the number, position, dimensions and a kind of a detected defect, for example, in case where the same sample is inspected, inspection of a large number of samples within a fixed time and the like.

In the technique described in the Patent Literatures 1 and 2, particularly minute defect having the dimension equal to or smaller than 20 nm, for example, cannot be detected since scattered light emitted from the defect is extremely low and a defect signal is buried in noise caused by scattered light emitted from the surface of the sample or noise of a detector or a detection circuit. Alternatively, in order to avoid it, when illumination power is increased, the temperature of the sample by illumination light is increased highly, so that thermal damage is caused to the sample. Alternatively, in order to avoid it, when the scanning speed of the sample is reduced, the area of the sample or the number of samples which can be inspected within a fixed time is reduced. As described above, it is difficult to detect the minute defect at a high speed.

As a method of detecting low light, a photon counting method is known. Generally, the photon counting in which the number of detected photons for low light is counted is performed to thereby improve the SN ratio of signal and accordingly the stable signal with high sensitivity and high accuracy can be obtained. As an example of the photon counting method, there is known a method of counting the occurrence number of pulse currents generated in response to incidence of photons on a photomultiplier or avalanche photodiodes. When plural photons enter or impinge in a short time and the pulse currents are generated plural times, it is impossible to count the pulse currents and accordingly an amount of light cannot be measured with high accuracy and the method cannot be applied to the defect inspection.

Further, as a method of another photon counting method, there is known a method of measuring the total of pulse currents generated in response to incidence of photons on pixels of a detector having a large number of avalanche photodiode pixels arranged. This detector is named Si-PM (Silicon Photomultiplier), PPD (Pixelated Photon Detector) or MPPC (Multi-Pixel Photon Counter). According to this method, the light amount can be measured even when plural photons enter in a short time as different from the photon counting using the above single photomultiplier or the avalanche photodiodes. However, since the large number of arranged avalanche photodiodes are operated as a detector having one "pixel", this method cannot be applied to the high-speed or high-sensitive defect inspection due to parallel detection of plural pixels.

Solution to Problem

In order to solve the above problems, the structure described in the Claims is adopted, for example.

The present invention includes plural measures for solving the above problems and an example thereof is described as follows: an illumination light adjustment step of adjusting light emitted from a light source to light flux having desired light amount, position, beam diameter and polarization state, an illumination intensity distribution control step of leading the light flux obtained in the illumination light adjustment step to a surface of a sample with a desired incident angle and forming illumination intensity distribution which is long in one direction and short in a direction perpendicular to the one direction on the surface of the sample, a sample scanning step of displacing the sample in a direction substantially perpendicular to a longitudinal direction of the illumination intensity distribution in an illumination tight irradiation position on the surface of the sample by the illumination intensity distribution control step, a scattered light detection step of counting the number of photons of scattered light emitted from plural small areas in an area irradiated with illumination light by the illumination intensity distribution control step in the sample scanning step to produce plural scattered light detection signals corresponding to the plural small areas, a defect judgment step of processing the plural scattered light detection signals obtained in the scattered light detection step to judge presence of a defect, a defect dimension judgment step of processing the scattered light detection signal relevant to each place in which the defect is judged to be present in the defect judgment step to judge dimensions of the defect and a display step of displaying position on the surface of the sample for each place in which the defect is judged to be present in the defect judgment step and the dimensions of the defect obtained in the defect dimension judgment step are provided.

Advantageous Effects of Invention

According to the present invention, there can be provided a defect inspection method, a low light detecting method and a low light detector which can scan all surface of a sample in a short time to detect a minute defect while reducing thermal damage caused to the sample, can calculate dimensions of the detected defect with high accuracy and can produce stable inspection result.

Other problems, structures and effects except the above will be apparent from the following description of embodiments.

DESCRIPTION OF EMBODIMENTS

Figure 1:
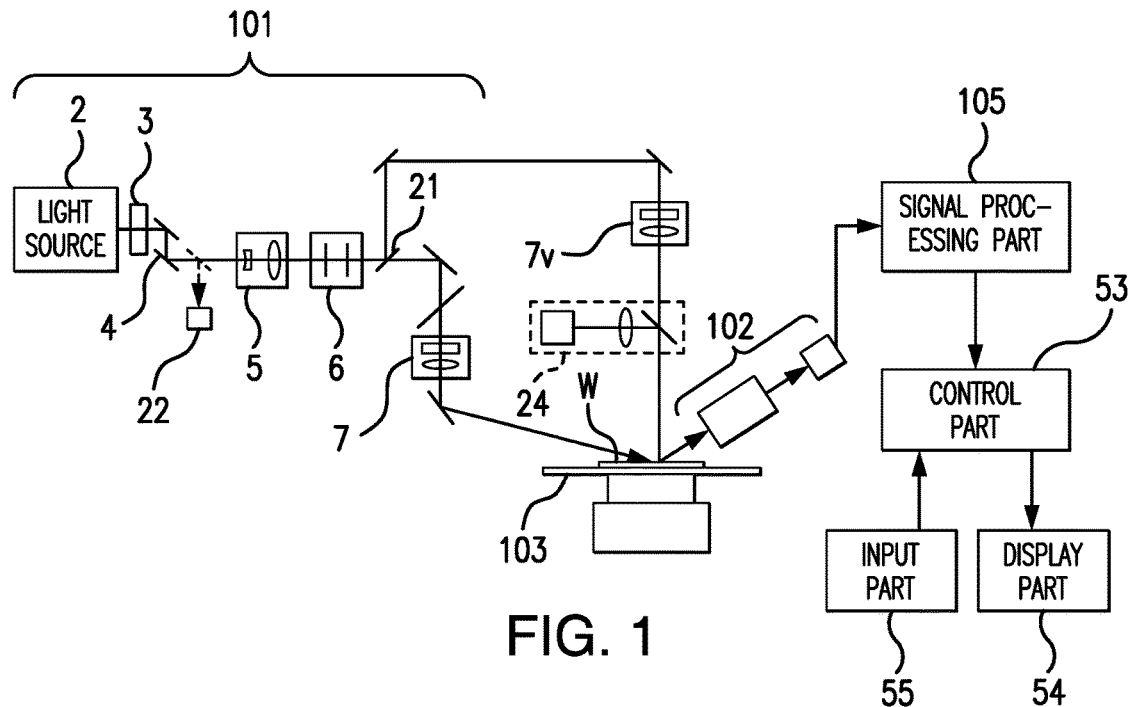
FIG. 1 is a schematic diagram illustrating the whole structure of an embodiment of a defect inspection device according to the present invention.

FIG. 1 shows an example schematically illustrating the embodiment. There are provided an illumination part 101, a detection part 102, a stage 103 on which a sample W can be put, a signal processing part 105, a control part 53, a display part 54 and an input part 55. The illumination part 101 includes a laser light source 2, an attenuator 3, an emitted light adjustment part 4, a beam expander 5, a polarization control part 6 and an illumination intensity distribution control part 7. A laser light beam emitted from the laser light source 2 is adjusted to a desired beam intensity by the attenuator 3 to enter the emitted light adjustment part 4 in which the adjusted light beam is further adjusted to have desired beam position and beam traveling direction. The light beam adjusted by the adjustment part 4 is adjusted to have a desired beam diameter by the beam expander 5 and further adjusted to have a desired polarization state by the polarization control part 6. The light beam adjusted by the polarization control part 6 is adjusted to have desired intensity distribution by the illumination intensity distribution control part 7 and to illuminate an inspection target area of the sample W.

An incident angle of the illumination light on the surface of the sample is decided by a position and an angle of reflecting mirrors of the emitted light adjustment part 4 disposed in an optical path of the illumination part 101. The incident angle of the illumination light is set to an angle suitable for detection of a minute defect. As the incident angle of the illumination light is larger, that is, as the elevation angle of the illumination light (angle between the sample surface and an optical axis of the illumination light)

is smaller, scattered light (named haze) from minute unevenness on the surface of the sample which is noise to scattered light from minute foreign matter on the sample surface is weak and accordingly it is suitable for detection of the minute defect. For this reason, when the scattered light from the minute unevenness on the sample surface disturbs detection of the minute defect, the incident angle of the illumination light may be preferably set to be equal to or larger than 75 degrees (equal to or smaller than 15 degrees for the elevation angle). On the other hand, as the incident angle of the illumination light is smaller in the obliquely incident illumination, an absolute amount of scattered light from minute foreign matter is larger and accordingly when insufficiency of an amount of scattered light from the defect disturbs detection of the minute defect, the incident angle of the illumination light may be preferably set to be equal to or larger than 60 degrees and equal to or smaller than 75 degrees (equal to or larger than 15 degrees and equal to or smaller than 30 degrees for the elevation angle). Further, when the obliquely incident illumination is performed, the polarization of the illumination light is set to P polarization by polarization control in the polarization control part 6 of the illumination part 101, so that the scattered light from the defect on the sample surface is increased as compared with other polarization. Moreover, when the scattered light from minute unevenness on the sample surface disturbs detection of the minute defect, the polarization of the illumination light is set to S polarization, so that the scattered light from the minute unevenness on the sample surface is reduced as compared with other polarization.

Further, if necessary, as shown in FIG. 1, a mirror 21 is inserted in the optical path of the illumination part 101 and other mirrors are disposed properly to thereby change the optical path of the illumination light, so that the sample surface is irradiated with the illumination light in the substantially perpendicular direction to the sample surface (perpendicular illumination). At this time, the illumination intensity distribution on the sample surface is controlled by an illumination intensity distribution control part 7v similarly to the obliquely incident illumination. In order to obtain scattered light from a hollow defect (scratch in grinding or crystal defect in crystal material) on the sample surface and the obliquely incident illumination by inserting a beam splitter in the same position as the mirror 21, the vertical illumination in which the illumination light enters the sample surface substantially perpendicularly thereto is suitable. Further, an illumination intensity distribution monitor 24 shown in FIG. 1 is described later in detail.

As the laser light source 2, a laser light source which generates an ultraviolet or vacuum ultraviolet laser beam having a short wavelength (equal to or smaller than 355 nm) as the wavelength difficult to penetrate into the sample and has high output equal to or larger than 2 W is used in order to detect the minute defect near the sample surface. A diameter of the emitted light beam is about 1 mm. In order to detect a defect in the sample, a laser light source which generates visible or infrared laser beam as a wavelength easy to penetrate into the sample is used.

The attenuator 3 includes a first polarizing plate, a half-wave plate which is rotatable about the optical axis of the illumination light and a second polarizing plate. Light which enters the attenuator 3 is converted into linearly polarized light by the first polarizing plate and the polarization direction thereof is rotated in any direction in accordance with an azimuth angle of a slow axis of the half-wave plate. The light having the polarization direction rotated passes through the second polarizing plate. The azimuth angle of the half-wave plate is controlled to thereby reduce the light intensity at any ratio. When the linear polarization degree of the light entering the attenuator 3 is sufficiently high, the first polarizing plate is not necessarily required. The attenuator 3 in which the relation between the input signal and the light reduction ratio is previously calibrated is used. As the attenuator 3, an ND filter having gradation concentration distribution can be also used or ND filters having plural concentrations different from one another can be also switched to be used.

The emitted light adjustment part 4 includes plural reflecting mirrors. In the embodiment, the emitted light adjustment part 4 composed of two reflecting mirrors is described, although the emitted light adjustment part 4 is not limited thereto and the emitted light adjustment part 4 may use three or more reflecting mirrors. Here, it is assumed that the three-dimensional orthogonal coordinate system (XYZ coordinates) is defined and incident light on the reflecting mirror travels in +X direction. The first reflecting mirror is installed to deflect the incident light in +Y direction (incidence and reflection in XY planes) and the second reflecting mirror is installed to deflect light reflected by the first reflecting mirror in +Z direction (incidence and reflection in YZ planes). A position and a traveling direction (angle) of light emitted from the emitted light adjustment part 4 are adjusted by means of parallel movement and adjustment of the elevation angle of the respective mirrors. As described above, the first and second reflecting mirrors are disposed so that incidence and reflection planes (XY planes) of the first reflecting mirror and incidence and reflection planes (YZ planes) of the second reflecting mirror are orthogonal with each other to thereby make it possible to adjust the position and the angle in XZ planes and the position and the angle in YZ planes of light (traveling in +Z direction) emitted from the emitted light adjustment part 4.

The beam expander 5 includes two or more lens groups and has the function of enlarging a diameter of incident parallel light flux. For example, a beam expander of Galileo type having a concave lens and a convex lens in combination is used. The beam expander 5 is installed on a translation stage having two or more axes and can adjust the position thereof so that the center thereof is identical with a predetermined beam position. Further, the beam expander 5 has the elevation angle adjustment function of the whole beam expander 5 so that the optical axis of the beam expander 5 is identical with a predetermined beam optical axis. A space between lenses can be adjusted to control an enlargement ratio of a diameter of the light flux (zoom mechanism). When light incident on the beam expander 5 is not parallel, enlargement of the diameter and collimation (quasi-collimation of light flux) of the light flux are performed at the same time by adjustment of the space between lenses. The collimation of the light flux may be made by installing a collimating lens independent of the beam expander 5 at the upper stream of the beam expander 5. The enlargement ratio of the beam diameter by the beam expander 5 is about 5 to 10 times and the light beam emitted from the light source and having a diameter of 1 mm is enlarged from 5 mm to 10 mm.

The polarization control part 6 is composed of a half-wave plate and a quarter-wave plate and controls the polarization state of the illumination light to any polarization state. State of light incident on the beam expander 5 and the illumination intensity distribution control part 7 is measured by a beam monitor 22 on the way of the optical path of the illumination part 101.

Figure 2:
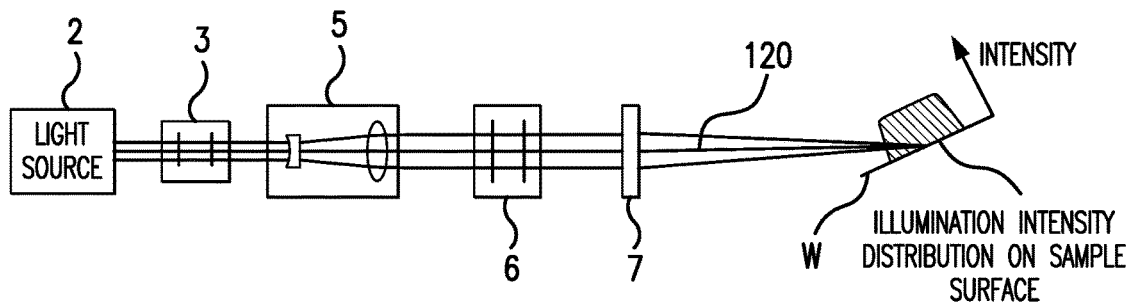
FIG. 2 is a diagram showing a first example of an illumination intensity distribution shape realized by an illumination part according to the present invention.
Figure 3:
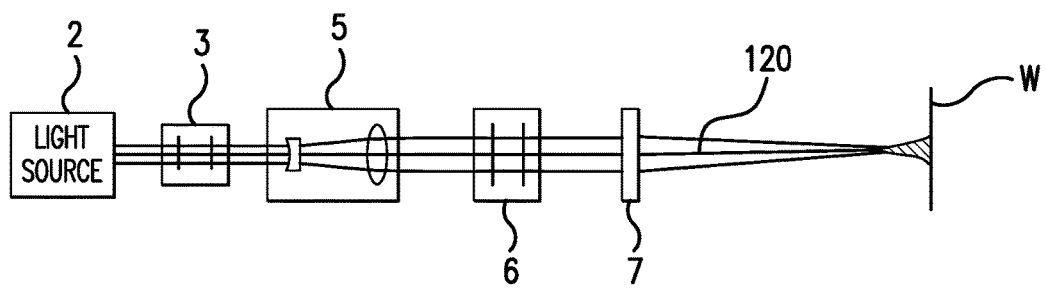
FIG. 3 is a diagram showing a second example of an illumination intensity distribution shape realized by the illumination part according to the present invention.
Figure 4:
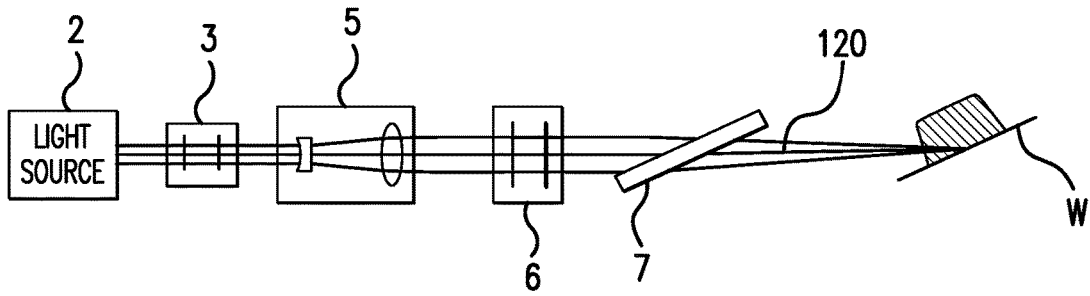
FIG. 4 is a diagram showing a third example of an illumination intensity distribution shape realized by the illumination part according to the present invention.
Figure 5:
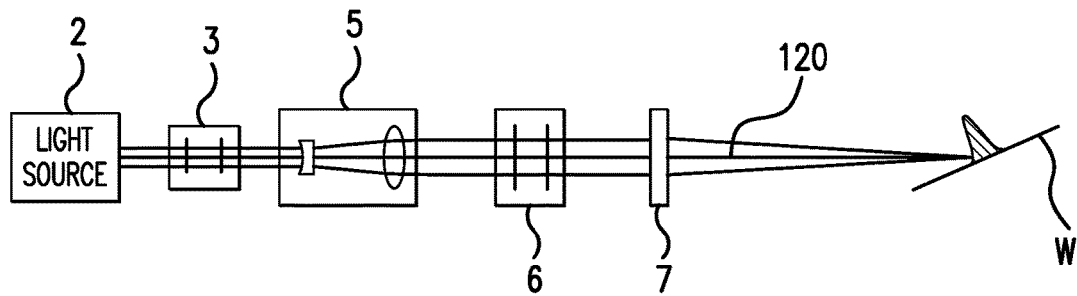
FIG. 5 is a diagram showing a fourth example of an illumination intensity distribution shape realized by the illumination part according to the present invention.
Figure 6:
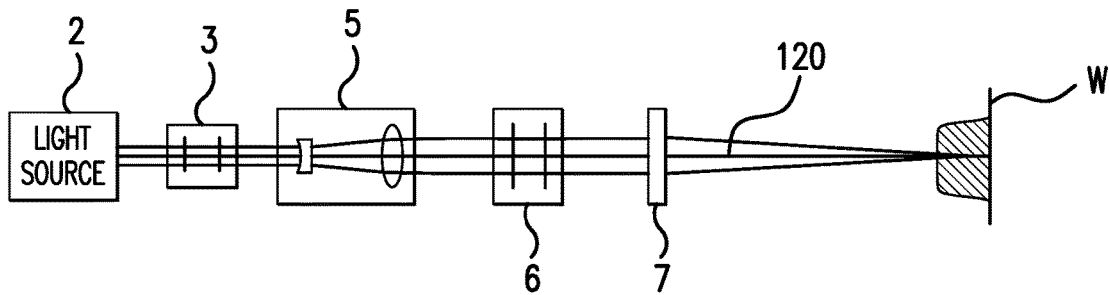
FIG. 6 is a diagram showing a fifth example of an illumination intensity distribution shape realized by the illumination part according to the present invention.

FIGS. 2 to 6 schematically illustrate the positional relation between an illumination optical axis 120 led to the sample surface by the illumination part 101 and the illumination intensity distribution shape. The structure of the illumination part 101 in FIGS. 2 to 6 shows part of the structure of the illumination part 101, and the emitted light adjustment part 4, the mirror 21, the beam monitor 22 and the like are omitted. FIG. 2 schematically illustrates a section of an incident plane of obliquely incident illumination (containing illumination optical axis and a normal line to the sample surface). The obliquely incident illumination is oblique to the sample surface in the incident plane. The substantially uniform illumination intensity distribution is formed in the incident plane by the illumination part 101. The length of part where the illumination intensity is uniform is about 100 µm to 4 mm since wide area per unit time is inspected. FIG. 3 schematically illustrates a section of a plane containing the normal line to the sample surface and perpendicular to the incident plane of the obliquely incident illumination. The illumination intensity distribution on the sample surface in the plane has the peripheral part in which the intensity is weak as compared with the center. More particularly, the illumination intensity distribution is the Gaussian distribution in which the intensity distribution of light incident on the illumination intensity distribution control part 7 is reflected or the intensity distribution similar to first-class first-degree Bessel function in which an opening shape of the illumination intensity distribution control part 7 is reflected or sine function. The length of the illumination intensity distribution (length of area having the illumination intensity equal to or larger than 13.5% of the maximum illumination intensity) in the plane is shorter than the length of part where the illumination intensity in the incident plane is uniform and is about 2.5 µm to 20 µm since haze generated from the sample surface is reduced. The illumination intensity distribution control part 7 includes optical elements such as aspheric lens, diffractive optical element, cylindrical lens array and light pipe described later. The optical elements constituting the illumination intensity distribution control part 7 are installed perpendicularly to the illumination optical axis as shown in FIGS. 2 and 3.

Figure 7:
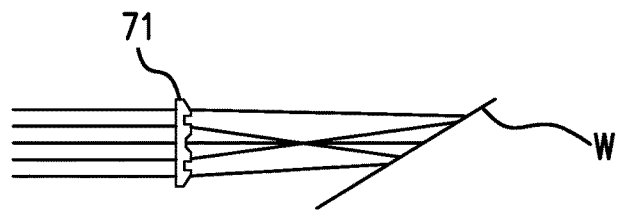
FIG. 7 is a diagram showing a first example of an optical element included in an illumination intensity distribution control part according to the present invention.

The illumination intensity distribution control part 7 includes an optical element acting on the phase distribution and the intensity distribution of incident light. A diffractive optical element (DOE) 71 is used (FIG. 7) as the optical element constituting the illumination intensity distribution control part 7. The diffractive optical element 71 includes minute undulating shape having a size equal to or smaller than the wavelength of light and formed on the surface of a substrate made of material which transmits the incident light. Molten quartz is used for ultraviolet rays as the material which transmits the incident light. In order to suppress attenuation of light caused by passage of the diffractive optical element 71, it is better to use the diffractive optical element subjected to coating using a reflection prevention film. The lithography method is used to form the minute undulating shape. When light which becomes quasi-collimated light after passage of the beam expander 5 passes through the diffractive optical element 71, the illumination intensity distribution is formed on the sample surface in accordance with the undulating shape of the diffractive optical element 71. The undulating shape of the diffractive optical element 71 is designed and manufactured to have a shape requested on the basis of calculation using the Fourier optical theory so that the illumination intensity distribution formed on the sample surface is long and uniform distribution in the incident plane. The optical element included in the illumination intensity distribution control part 7 is provided with a translation adjustment mechanism having two or more axes and a rotation adjustment mechanism having two or more axes so that relative position and angle of the incident light to the optical axis can be adjusted. Furthermore, a focus adjustment mechanism using movement in the optical axis direction is provided. As a substitute optical element having the same function as the diffractive optical element 71, an aspheric lens, a combination of cylindrical lens array and cylindrical lens and a combination of light pipe and focusing lens may be used.

The state of illumination light in the illumination part 101 is measured by the beam monitor 22. The beam monitor 22 measures position and angle (in the traveling direction) of the illumination light passing through the emitted light adjustment part 4 or position and wave surface of the illumination light incident on the illumination intensity distribution control part 7 to be outputted. The measurement of position of the illumination light is made by measuring the position in the center of gravity of light intensity of the illumination light. As a concrete position measurement means, a position sensitive detector (PSD) or an image sensor such as CCD sensor and CMOS sensor is used. The measurement of angle of the illumination light is made by an optical position sensor or an image sensor installed in a position far distant from the light source than the position measurement means or in a focused position of the collimating lens. The position and the angle of illumination light measured by the beam monitor 22 are supplied to the control part 53 to be displayed in the display part 54. When the position or the angle of illumination light is shifted from a predetermined position or angle, the emitted light adjustment part 4 adjusts the position or the angle of illumination light to be returned to predetermined position.

The measurement of wave surface of the illumination light is made in order to measure a parallel degree of light incident on the illumination intensity control part 7. Measurement using a sharing interferometer or a Shack Hartman wave surface sensor is performed. The sharing interferometer includes optical glass having both sides polished evenly and a thickness of about several mm and which is inserted in the optical path of the illumination light obliquely and measures emanation and convergence states of the illumination light by pattern of interference fringes observed when reflected light from the surface and reflected light from the back are projected on a screen. As the sharing interferometer, there is SPUV-25 made by a SIGMA KOKI Co., Ltd. or the like. When an image sensor such as CCD sensor and CMOS sensor is disposed in a screen position, the emanation and convergence states of the illumination light can be measured automatically. The Shack Hartman wave surface sensor includes a small lens array which divides wave surface to project divided wave surfaces on an image sensor such as CCD sensor and measures inclination of individual wave surfaces from displacement of the projection position. Detailed measurement of wave surface such as disturbance of partial wave surface can be made as compared with the sharing interferometer. When it becomes clear from the measurement of wave surface that light incident on the illumination intensity control part 7 is not quasi-collimated light and is emanated or converged, a lens group of the beam expander 5 at a pre-stage can be displaced in the optical axis direction to approach the quasi-collimated light. Further, when it becomes clear from the measurement of wave surface that the wave surface of light incident on the illumination intensity control part 7 is partially inclined, a spatial light phase modulation element which is a kind of a spatial light modulator (SLM) can be inserted in the prestage of the illumination intensity control part 7 to give proper phase difference to each position of the section of light flux so that the wave surface is even to thereby make the wave surface approach to be even, that is, make the illumination light approach the quasi-collimated light. The accuracy of wave surface (shift from the predetermined wave surface (design value or initial state) of light incident on the illumination intensity distribution control part 7 can be suppressed to $\lambda/10$ rms or less by means of the wave surface accuracy measurement and adjustment means described above.

The illumination intensity distribution on the sample surface adjusted by the illumination intensity distribution control part 7 is measured by the illumination intensity distribution monitor 24. Further, as shown in FIG. 1, even when the vertical illumination is used, the illumination intensity distribution on the sample surface adjusted in the illumination intensity distribution control part 7v is measured by the illumination intensity distribution monitor 24 similarly. The illumination intensity distribution monitor 24 focuses the sample surface on an image sensor such as CCD sensor and CMOS sensor through a lens to be detected as an image. The image of the illumination intensity distribution detected by the illumination intensity distribution monitor 24 is processed in the control part 53 so that a position of the center of gravity, of intensity, a maximum intensity, a position of the maximum intensity, width and length of the illumination intensity distribution (width and length of the illumination intensity distribution area exceeding predetermined intensity or predetermined ratio to the maximum intensity value) and the like are calculated to be displayed in the display part 54 together with an outline shape and a sectional shape of the illumination intensity distribution.

Figure 8:
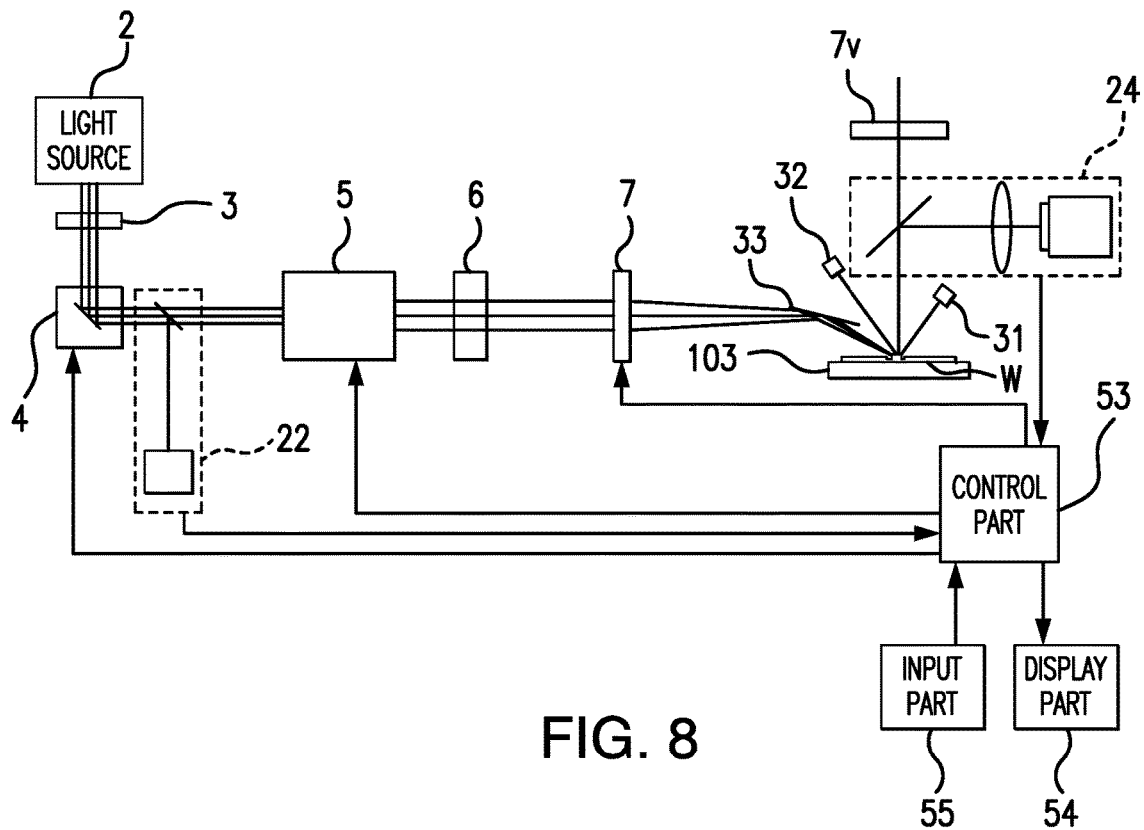
FIG. 8 is a diagram showing an example of an embodiment of measurement means and adjustment means for state of illumination light in an illumination part according to the present invention.

When the obliquely incident illumination is made, positional displacement of the illumination intensity distribution due to displacement in height of the sample surface and disturbance of the illumination intensity distribution due to defocusing occur. In order to suppress it, the height of the sample surface is measured and when the height is shifted, the shift is corrected by the illumination intensity distribution control part 7 or adjustment of the height in the Z axis of the stage 103. FIG. 8 schematically illustrates an example of the illumination part and the part concerning measurement and correction of the illumination light of the embodiment. The height of the sample surface is measured by means of a light beam emission part 31 and a light receiving part 32 which receives light emitted from the light beam emission part 31 and reflected on the sample surface. The light beam emission part 31 includes a light source such as a semiconductor laser and a floodlighting lens. The light receiving part 32 includes a light receiving lens and an optical position sensor. Since the sample surface having strong gloss such as the surface of a semiconductor silicon and the surface of a magnetic disk substrate or board is measured, the light beam emission part 31 and the light receiving part 32 are disposed so that light emitted from the light beam emission part 31 and regularly reflected on the sample surface can be received by the light receiving part 32. The displacement of height of the sample surface is detected as positional shift of a light spot detected by the optical position sensor of the light receiving part 32 using the theory of triangular surveying.

The positional shift in the in-plane direction of the sample surface of the illumination light irradiation position due to the displacement in height of the sample surface is corrected by adjustment of deflection angle by deflection means 33 which is disposed downstream of the illumination intensity distribution control part 7 and directs the illumination light to the sample surface. The deflection means 33 includes a reflecting mirror which deflects the illumination light and a piezo element which controls the elevation angle to the optical axis of the illumination light of the reflecting mirror. The deflection means 33 controls the elevation angle within a range of about ±1 mrad by using a frequency of 400 Hz or more. The positional shift in the in-plane direction of the sample surface of the illumination light irradiation position is calculated from the measurement value of displacement in height and the incident angle of the illumination light and a control signal outputted from the control part 53 is received by the deflection means 33 to control the reflecting mirror so that the shift is corrected. The positional shift in the in-plane direction of the sample surface of the illumination light irradiation position can be also corrected by directly measuring the position of the center of gravity of the illumination intensity distribution using the illumination intensity distribution monitor 24. When the positional shift in the in-plane direction of the sample surface of the illumination light irradiation position due to displacement in height of the sample surface is corrected by the deflection means 33, the length of optical path between the illumination intensity distribution control part 7 and the sample surface is deviated or differentiated as compared with the state that the correction is not made and accordingly defocusing of an illumination spot occurs depending on the shift amount. The shift amount of the length of optical path is calculated from the measurement value of displacement in height and the incident angle of the illumination light and the defocusing is reduced by positional adjustment in the optical axis direction of the optical element provided in the illumination intensity distribution control part 7 or adjustment of emanation angle of the beam expander 5 on the basis of the calculated shift amount.

Figure 10:
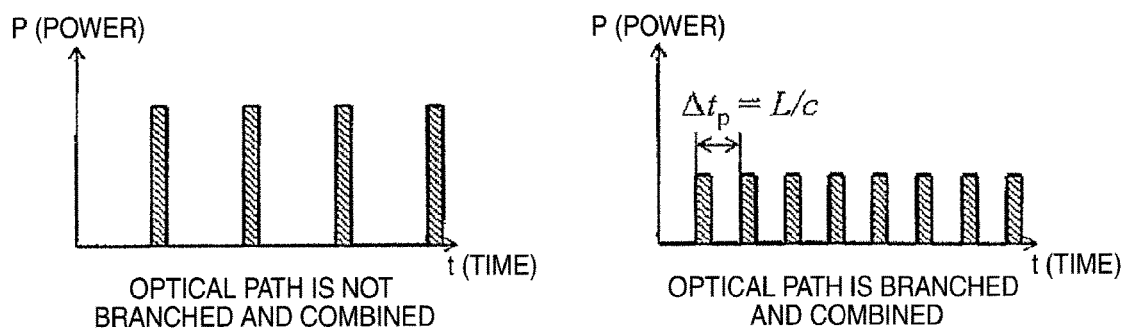
FIG. 10 is a diagram showing energy reduction result per single pulse by the division and the combination of optical paths.

When a pulse laser which is easy to produce high output is used as the light source 2, illumination energy given to the sample is concentrated in a moment that pulse is inputted and accordingly the sample is sometimes subjected to thermal damage caused by instantaneously increased temperature due to inputting of the pulse. In order to avoid it, the optical path of the pulse laser is branched or divided and a difference is given between the branched optical paths. Then, the branched optical paths are combined, so that energy per one pulse can be reduced effectively while the total energy is maintained as shown in FIG. 10.

Figure 9:
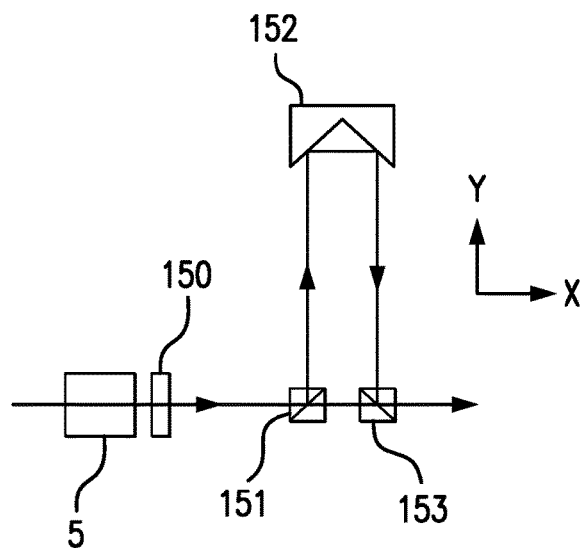
FIG. 9 is a diagram showing an example of means for reducing energy per single pulse by division and combination of optical paths in the illumination part according to the present invention.

FIG. 9 shows an example of an optical system for implementing the above operation. The illumination light passing through the beam expander 5 is branched or divided by a polarizing beam splitter 151 into light passing through a first optical path formed by reflecting the light by the polarizing beam splitter 151 and light passing through a second optical path formed by light passing through the polarizing beam splitter 151. Light passing through the first optical path is reflected by a retroreflector 152 to be returned and is then reflected by a polarizing beam splitter 153 to be combined with light passing through the second optical path. The retroreflector 152 includes two or more reflecting mirrors orthogonal with each other and returns input light in the opposite direction of 180 degrees. The retroreflector is also named a corner cube. Two or more independent reflecting mirrors may be used instead of the retroreflector. In order to make the intensity of the light reflected by the polarizing beam splitter 151 equal to the intensity of the light passing through the polarizing beam splitter, a wave plate 150 is used to adjust polarization of the illumination light to be circular polarization or linear polarization of 45 degrees in inclination. When the difference between the first and second optical paths is L, the time interval between a pulse of light passing through the first optical path and a pulse of light passing through the second optical path is $\Delta tp=t/c$. The time interval $\Delta tp$ is made equal to or larger than the time required to suppress increase of temperature at the time that a single pulse is inputted, so that instantaneous increase of temperature of the sample by the single pulse and increase of temperature due to thermal accumulation by plural pulses can be suppressed.

Figure 11:
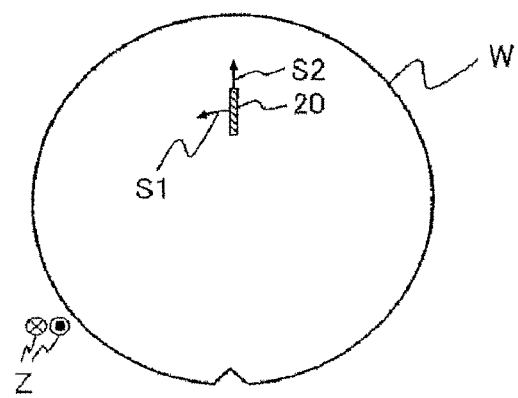
FIG. 11 is a diagram showing an illumination distribution shape and a scanning direction on the surface of a sample according to the present invention.
Figure 12:
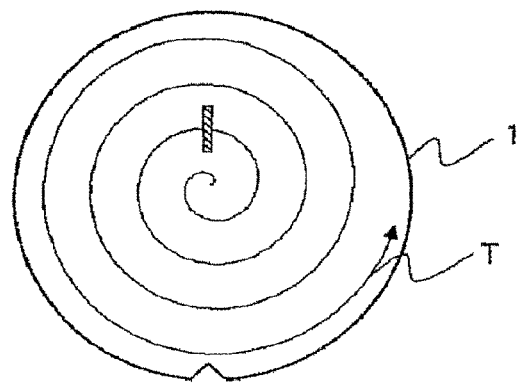
FIG. 12 is a diagram showing a locus of an illumination spot by scanning.

Referring to FIGS. 11 and 12, an illumination distribution shape (illumination spot 20) formed on the sample surface by the illumination part 101 and a sample scanning method are described. A circular semiconductor silicon wafer is supposed as the sample W. The stage 103 includes a translation stage, a rotation stage and a Z stage for adjustment of height of the sample surface (all not shown). The illumination spot 20 has the illumination intensity distribution which is long in one direction as described above and the direction thereof is S2. The direction that is substantially orthogonal to the direction S2 is supposed to S1. Scanning is made in the circumferential direction S1 of a circle having a rotation axis of the rotation stage as the center thereof by rotation motion of the rotation stage and in the translational direction S2 of the translation stage by translation motion of the translation stage. The scanning is made by the length equal to or shorter than the length in the longitudinal direction of the illumination spot 20 in the scanning direction S2 while the sample makes one rotation by scanning in the scanning direction S1, so that a spiral locus T is drawn on the sample W by the illumination spot to thereby scan the whole surface of the sample 1.

Figure 13:
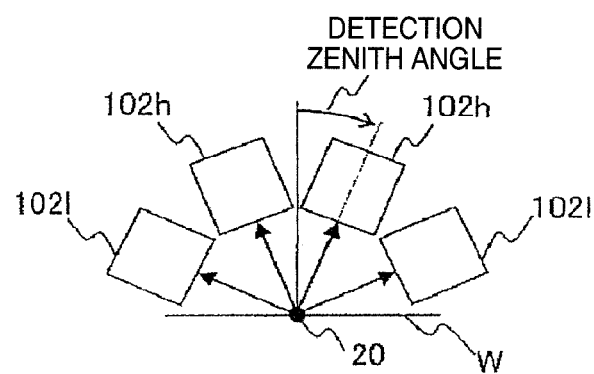
FIG. 13 is a diagram as viewed from the side and showing arrangement and detection directions of detection parts according to the present invention.
Figure 14:
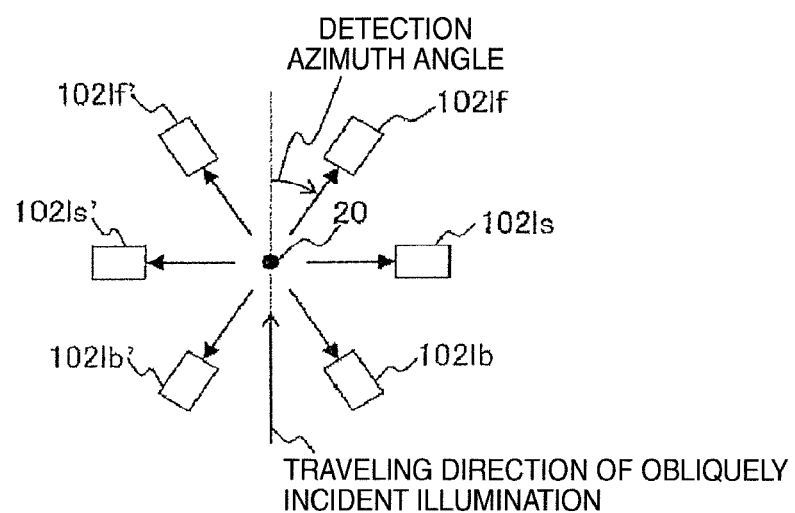
FIG. 14 is a diagram as viewed from the upper side and showing arrangement and detection directions of low-angle detection parts according to the present invention.
Figure 15:
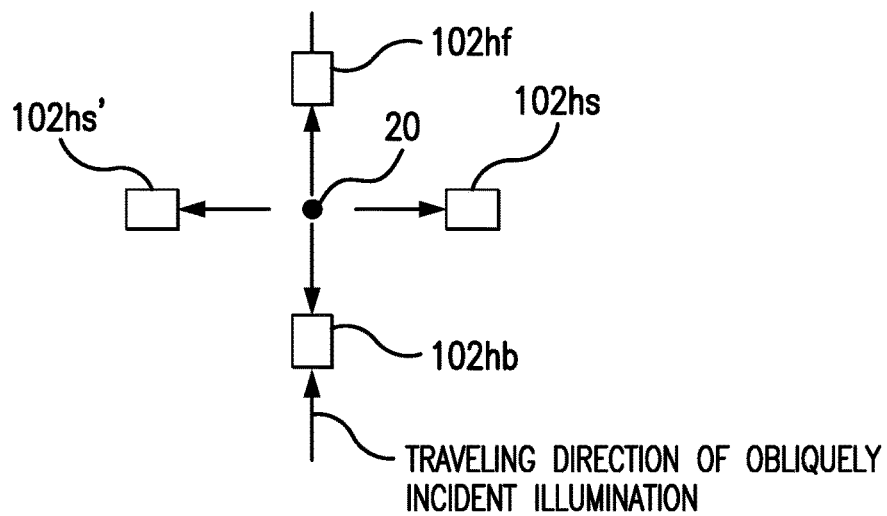
FIG. 15 is a diagram as viewed from the upper side and showing arrangement and detection directions of high-angle detection parts according to the present invention.

The plural detection parts 102 are disposed to detect scattered light in plural directions emitted from the illumination spot 20. An example of arrangement of the sample W and the illumination spot 20 in the detection part 102 is described with reference to FIGS. 13 to 15. FIG. 13 is a side view showing arrangement of the detection parts 102. An angle of a detection direction (the central direction of detection opening) by the detection part 102 to the normal line of the sample W is defined as a detection zenith angle. The detection parts 102 include high-angle detection parts 102h having the detection zenith angle of 45 degrees or less and low-angle detection parts 102l having the detection zenith angle of 45 degrees or more. The high-angle detection parts 102h and the low-angle detection parts 102l each include plural detection parts so that light scattered in numerous directions in each detection zenith angle is covered. FIG. 14 is a plan view showing arrangement of the low-angle detection parts 102l. An angle between the traveling direction of the obliquely incident illumination and the detection direction in the plane parallel to the surface of the sample W is defined as a detection azimuth angle. The low-angle detection parts 102 include a low-angle front detection part 102lf, a low-angle side detection part 102ls and a low-angle back detection part 102lb and further the low-angle detection parts 102 include a low-angle front detection part 102lf', a low-angle side detection part 102ls' and a low-angle back detection part 102lb' arranged in symmetrical positions with respect to the above detection parts 102lf, 102ls and 102lb in the illumination incident plane, respectively. For example, the low-angle front detection part 102lf is installed to have the detection azimuth angle equal to or larger than 0 degree and equal to or smaller than 60 degrees, the low-angle side detection part 102ls is installed to have the detection azimuth angle equal to or larger than 60 degrees and equal to or smaller than 120 degrees, and the low-angle back detection part 102lb is installed to have the detection azimuth angle equal to or larger than 120 degrees and equal to or smaller than 180 degrees. FIG. 15 is a plan view showing arrangement of the high-angle detection parts 102h. The high-angle detection parts 102 include a high-angle front detection part 102hf, a high-angle side detection part 102hs, a high-angle back detection part 102hb and a high-angle side detection part 102hs' arranged in a symmetrical position with respect to the high-angle side detection part 102hs in the illumination, incident plane. For example, the high-angle front detection part 102hf is installed to have the detection azimuth angle equal to or larger than 0 degree and equal to or smaller than 45 degrees, the high-angle side detection part 102hs is installed to have the detection azimuth angle equal to or larger than 45 degrees and equal to or smaller than 135 degrees and the high-angle back detection part 102hb is installed to have the detection azimuth angle equal to or larger than 135 degrees and equal to or smaller than 180 degrees. Here, four high-angle detection parts 102h and six low-angle detection part 102l are provided, although the present invention is not limited thereto and the number and the position of the detection parts may be changed properly.

Figure 16:
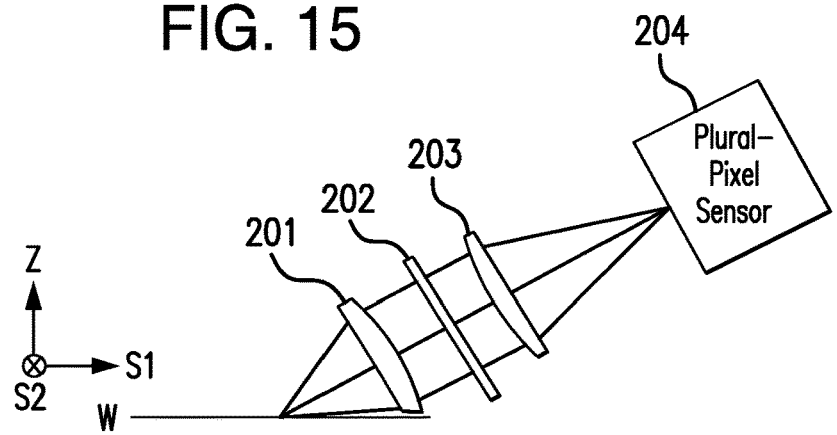
FIG. 16 is a diagram showing a first example of the structure of a detection part according to the present invention.

FIG. 16 shows an example illustrating the concrete structure of the detection part 102. The scattered light emitted from the illumination spot 20 is focused by an objective lens 201 and after the focused light passes through a polarizing filter 202, the light is led to light receiving plane of plural-pixel sensor 204 by a focusing lens 203 to be detected. In order to detect the scattered light efficiently, it is preferable that detection NA of the objective lens is equal to or larger than 0.3. In case of the low-angle detection part, a lower end of the objective lens 201 is cut off if necessary so that the lower end of the objective lens 201 does not interfere with the sample surface W. The polarizing filter 202 is constituted of a polarizing plate or polarizing beam splitter and is installed to cut linear polarization component in any direction. A wire grid polarizing plate or polarizing beam splitter having the transmission factor equal to or larger than 80% is used as the polarizing plate. When any polarization component containing elliptical polarization is cut, the polarizing filter 202 including a wave plate and a polarizing plate is installed.

Figure 18:
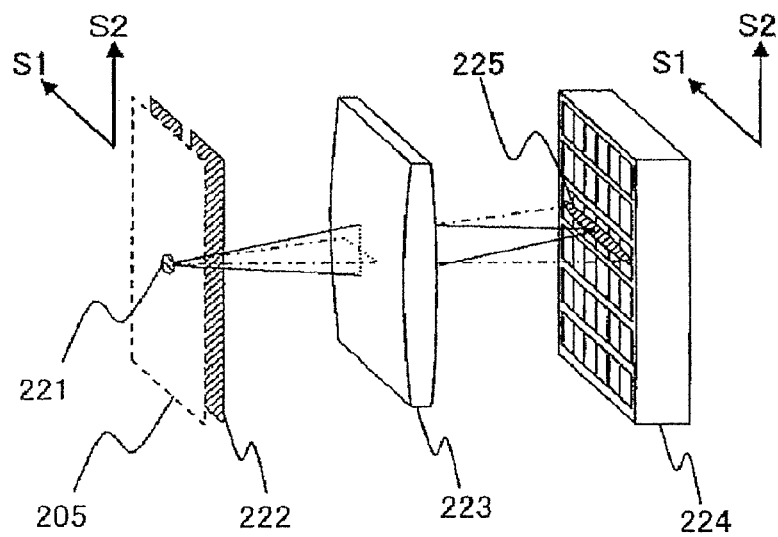
FIG. 18 is a diagram showing a first example of plural-pixel sensor of a detection part according to the present invention.

FIG. 18 schematically illustrates the structure of the plural-pixel sensor 204. An image of the sample surface is focused on a plane 205 conjugate to the sample surface by the objective lens 201 and the focusing lens 203. A defect image 221 and one-axis enlarged image 225 of the defect image in FIG. 18 schematically illustrate an example of the state in which the defect is positioned in the center of the visual field for detection of the detection part 102. After the defect image 221 is once focused on conjugate plane 225 to the sample surface, the defect image travels in the optical axis direction of the detection part 102 with spread angle conforming to NA on the image side of the focusing lens 203. This light beam is focused in the direction corresponding to the scanning direction S2 on the conjugate plane 205 to the sample surface by means of one-axis focusing system 223 to be focused on the light receiving plane of an array sensor 224. The light beam in the direction corresponding to the scanning direction S1 on the conjugate plane 205 to the sample surface reaches the light receiving plane of the array sensor 224 with the spread angle.

The one-axis focusing system 223 has the function that light is focused only in the direction corresponding to the scanning direction S1 and is composed of a cylindrical lens or a combination of cylindrical lens and spherical lens. The defect image 221 is spread or enlarged in the direction corresponding to the scanning direction S1 by the one-axis focusing system 223. A size of the defect image on the conjugate plane 205 to the sample surface is decided by the optical resolution degree of the detection part 102 in case of minute defect smaller than the wavelength of the illumination light and is concretely decided by NA on the image side of the focusing lens 203 (the size of image of the minute defect (spread point image)=1.22×(wavelength)/(NA on image side)). The length in the S1 direction of the one-axis enlarged image 225 of the defect image, that is, the enlargement ratio in the S1 direction is decided by the length of the optical path between the conjugate plane 205 to the sample surface and the light receiving plane of the array sensor 224 and NA on the image side of the focusing lens 203. The plural-pixel sensor 204 is constructed so that the length in the S1 direction of the one-axis enlarged image 225 of the defect image is substantially equal to the length in the S1 direction of the light receiving plane of the array sensor 224. The width in the S2 direction of the one-axis enlarged image 225 of the defect image is decided by magnification of the one-axis focusing system 223. The plural-pixel sensor 204 is constructed so that the length is equal to or shorter than the length in the S2 direction of the light receiving plane of the array sensor 224.

The scattered light from the sample surface is generated from position of the illumination spot 20 and detected by the detection part 102, although even an area on the outside of the illumination spot 20 is substantially irradiated with the illumination light having relatively weak intensity because of the wave motion nature of light. Consequently, there is a case where part of scattered light generated by large foreign matter on the outside of the illumination spot 20 or edge at an end of the sample surface enters the light receiving plane of the array sensor 224 and becomes noise to reduce the sensitivity. When this causes a problem, a shielding slit 222 can be disposed so that obstructive scattered light can be shielded to be reduced. The shielding slit has a slit opening (light transmission part) having the width wider than the width of image on the illumination spot 20 on the conjugate plane 205 to the sample surface and the shielding slit is disposed so that the center of the slit opening is identical with the position of the image on the illumination spot 20. Since the other area except the opening is shielded, the scattered light from the other area except the area on the sample surface on which the illumination spot 20 is impinged is reduced.

Figure 19:
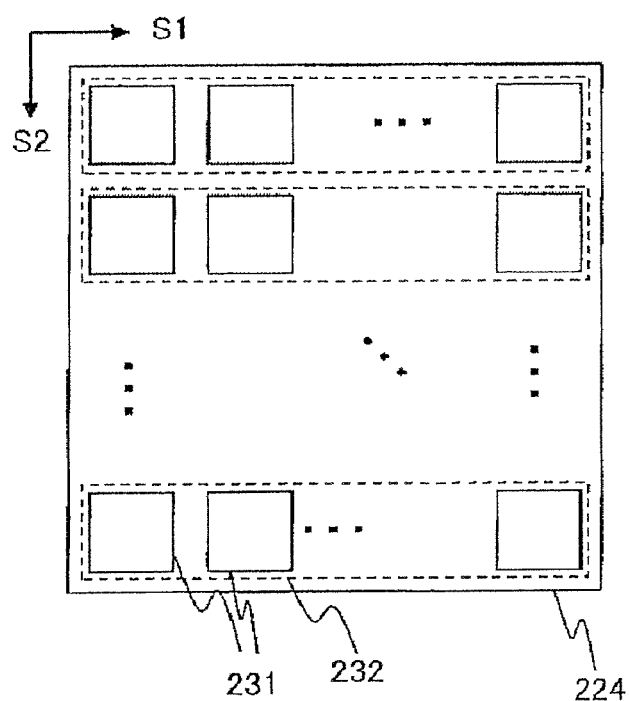
FIG. 19 is a diagram showing a first example of an array sensor in a detection part according to the present invention.

FIG. 19 shows an example schematically illustrating the light receiving plane of the array sensor 224. The array sensor 224 includes plural avalanche diodes (APD) arranged two-dimensionally. Hereinafter, each APD of the receiving part is named an APD pixel. APD pixels 231 each are applied with a voltage so that each of them is operated in the Geiger mode (photoelectron multiplication factor is equal to or larger than $10^5$). When one photon enters the APD pixel 231, photoelectrons are generated in the APD pixel 231 with the probability according to the quantum efficiency of the APD pixel and are multiplied by action of the APD in the Geiger mode, so that an electrical pulse signal is produced. An APD pixel row 232 in S1 direction (a collection of APD pixels enclosed by a quadrilateral 232 of broken line in FIG. 19) is defined as one unit and the electrical pulse signals generated in the APD pixels contained in the pixel row are totalized in each APD pixel row in the Si direction to be outputted. Plural APD pixel rows are arranged in S2 direction and output signals of the APD pixels in the plural rows are outputted in parallel.

Figure 20:
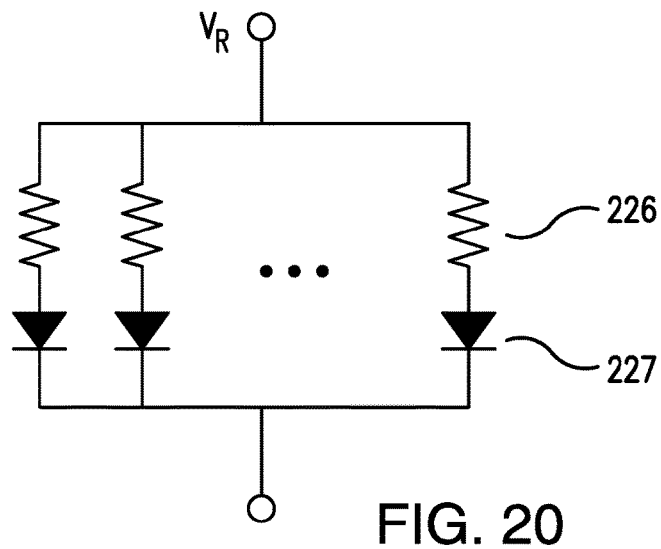
FIG. 20 is a diagram showing an equivalent circuit of constituent elements of the array sensor.

FIG. 20 shows an example of a circuit diagram equivalent to one APD pixel row 232 in the S1 direction. In FIG. 20, a pair of one quenching resistor 226 and APD 227 corresponds to one APD pixel 231. Each APD is applied with an reverse voltage $V_R$. The reverse voltage is set to be equal to or higher than a breakdown voltage of the APD so that the APD 227 is operated in the Geiger mode. With the circuit configuration shown in FIG. 20, an electrical output signal (peak value of voltage or current or electric charge amount) proportional to the total number of photons incident on the APD pixel row 232 in S1 direction is obtained. The electrical output signals (peak value of voltage or current or electric charge amount) corresponding to the APD pixel rows 232 in S1 direction are converted from analog signals to digital signals and outputted in parallel as the digital signal in time series.

The individual APD pixels output only the pulse signal to the same degree as in the case where one photon is incident even if plural photons are incident in a short time and accordingly when the number of incident photons per unit time on the individual APD pixels is increased, the total output signal of the APD pixel row is not proportional to the number of incident photons and the linearity of signal is deteriorated. Further, when incident light exceeding a fixed amount (about one photon on average per pixel) enters all pixels in the APD pixel row, an output signal is saturated. Arrangement of the large number of APD pixels in the Si direction can reduce the incident light amount per pixel and counting of photons can be made more correctly. For example, when the number of pixels in the S1 direction is 1000, sufficient linearity can be ensured with optical intensity equal to or smaller than about 1000 photons per unit time of detection in case where the quantum efficiency of APD pixels is 30% and the optical intensity equal to or smaller than about 3300 photons can be detected without saturation.

In the structure of the plural-pixel sensor 204 shown in FIG. 18, the optical intensity in the S1 direction is not uniform and the optical intensity at ends of the array sensor 224 is weak as compared with the center of the array sensor 224. This means that the number of effective APD pixels in the S1 direction is reduced. A lenticular lens composed of a lot of minute cylindrical lenses having the curvature in the S1 direction and arranged in the S1 direction instead of cylindrical lenses, diffraction-type optical elements or spherical lenses can be used to make the distribution in the S1 direction of the one-axis enlarged image 225 of the defect image have uniform intensity. By doing so, the optical intensity range in which the linearity can be ensured or the optical intensity range in which saturation does not occur can be extended while the number of APD pixels in the S1 direction is maintained.

With the structure of the plural-pixel sensor 204 described above, the number of photons at each position in the S2 direction on the conjugate plane 205 to the sample surface can be counted in parallel at the same time.

Figure 17:
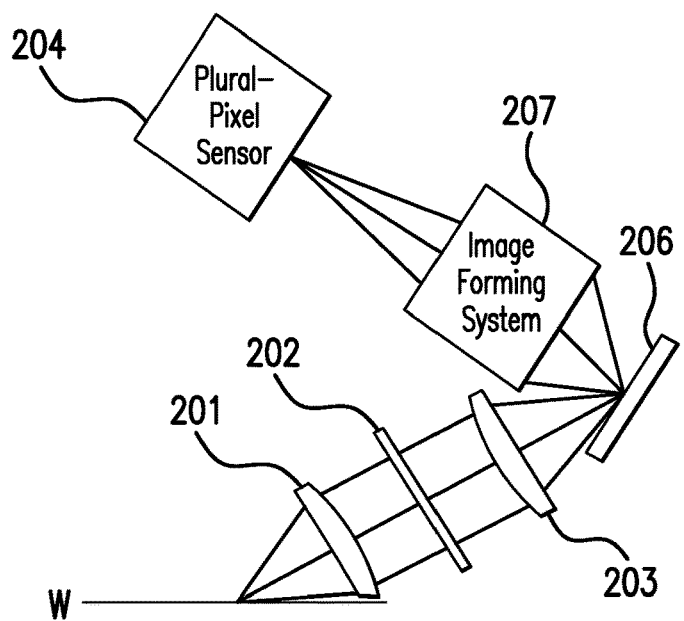
FIG. 17 is a diagram showing a second example of the structure of a detection part according to the present invention.

FIG. 17 shows a modification example illustrating the concrete structure of the detection part 102. The scattered light emitted from the illumination spot 20 is focused by the objective lens 201 and after the focused light passes through the polarizing filter 202, the light is focused on a diffraction grating 206 disposed on a plane conjugate to the sample surface to form an image (intermediate image) of the sample surface. The image of the sample surface formed on the diffraction grating 206 is projected on the light receiving plane of the plural-pixel sensor 204 by an image forming system 207 to be detected. The plural-pixel sensor 204 is disposed in the plane conjugate to the sample surface so that the arrangement direction of pixels is identical with the longitudinal direction of the image of the illumination spot 20 in accordance with the shape of the illumination spot 20 which is extended in one direction. As the diffraction grating 206, the diffraction grating having a formed diffraction grating shape is used so that Nth degree diffracted light of incident light along the optical axis of the light led by the focusing lens 203 to form the intermediate image is directed in the normal direction of the surface of the diffraction grating 206 in order to diffract the light led by the focusing lens 203 to form the intermediate image into the normal direction of the surface of the diffraction grating 206. In order to enhance the diffraction efficiency, a blaze diffraction grating is used. By disposing the plural-pixel sensor 204 on the plane conjugate to the sample surface with the above structure, deviation of focusing can be reduced even in the S1 direction on the sample surface to ensure effective visual field in the wide range and the scattered light can be detected with reduced loss in light amount.

The relation of the length of the illumination spot 20, the optical magnification of the detection part 102 and the dimension of the plural-pixel sensor 204 is described. When the high-sensitivity and high-speed inspection is performed, the length of the illumination spot 20 is set to about 500 μm. When the plural-pixel sensor 204 having 100 pixels arranged at intervals of 25 μm in the S2 direction (100 APD pixel rows 232 are arranged in the S1 direction) is installed, the optical magnification of the detection part is 5 times and the interval of pixels projected on the sample surface is 5 μm.

When the sample is rotated at the rotation speed of 2000 rpm on the above condition, all surface of a circular sample having a diameter of 300 mm is scanned in 9 seconds and all surface of a circular sample having a diameter of 450 mm is scanned in 14 seconds. Further, when inspection is performed at higher speed, the length of the illumination spot 20 is set to about 100 μm. In this case, the optical magnification of the detection part is 0.4 times and the interval of pixels projected on the sample surface is 62.5 μm. When the sample is rotated at the rotation speed of 2000 rpm on this condition, all surface of a circular sample having a diameter of 300 mm is scanned in 5 seconds and all surface of a circular sample having a diameter of 450 mm is scanned in 7 seconds.

Figure 21:
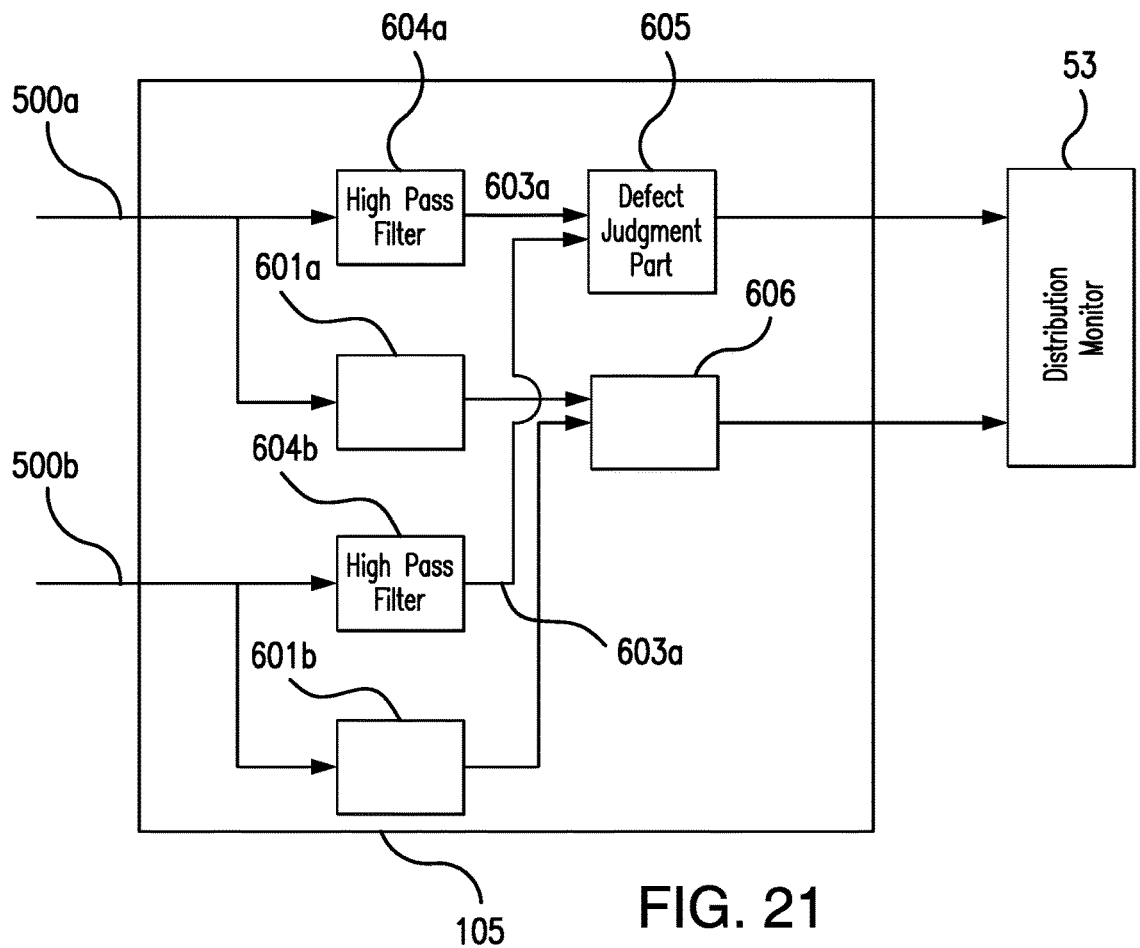
FIG. 21 is a diagram showing an embodiment of a signal processing part according to the present invention.

Next, referring to FIG. 21, a signal processing part 105 which classifies various kinds of defects and presumes dimensions of the defects with high accuracy on the basis of intensity detection signals of scattered light in various directions detected at the same time by plural detection optical systems which cover a wide angular range is described. Here, for the sake of simplicity, the structure of the signal processing part 105 having two systems of detection parts 102a and 102b (not shown) of plural detection parts 102 is described. Further, each of the detection parts 102a and 102b produces signal for each APD pixel row. Here, description is made while attention is paid to the signal of one pixel row thereof, although it is needless to say that the same processing is performed even for other pixel rows in parallel. Output signals 500a and 500b outputted from the detectors included in the detection parts 102a and 102b and corresponding to detected scattered light amounts are supplied to a digital processing part 52 in which defect signals 603a and 603b are extracted by high-pass filters 604a and 604b to be supplied to a defect judgment part 605. Since defects are scanned in the S1 direction by the illumination spot 20, the waveform of the defect signals is enlargement or reduction of an illumination distribution profile in the S1 direction of the illumination spot 20. Accordingly, the high-pass filters 604a and 604b are used to make the defect signal pass through a frequency band containing defect signal waveform to thereby cut the frequency band and the DC component containing much noise relatively, so that S/N of the defect signals 603a, 603b is improved. As the high-pass filters 604a, 604b, high-pass filters or band-pass filters designed to have a specific cut-off frequency and cut off the frequency component exceeding the frequency or FIR filters having a similar figure to the waveform of the defect signals on which the shape of the illumination spot 20 is reflected may be used. The defect judgment part 605 subjects input of signals containing the defect waveform outputted from the high-pass filters 604a, 604b to threshold processing to judge whether defect is present or not. That is, the defect judgment part 605 is supplied with the defect signals based on the detection signals from the plural detection optical systems and accordingly the defect judgment part 605 subjects the sum or the weighted average of plural defect signals to threshold processing or takes OR or AND of defect groups extracted by the threshold processing to which the plural defect signals are subjected on the same coordinate system set on the surface of wafer, so that the defects can be inspected with high sensitivity as compared with defect inspection based on a single defect signal.

Further, the defect judgment part 605 supplies defect coordinates indicating a defect position in the wafer and presumed values of dimensions of the defect calculated on the basis of the defect waveform and a sensitivity information signal in a place judged that the defect is present to the control part 53 as defect information to be outputted to the display part 54 or the like. The defect coordinates are calculated using the center of gravity of the defect waveform as a reference. The defect dimensions are calculated on the basis of an integrated value or a maximum value of the defect waveform.

Moreover, output signals from analog processing part 51 are supplied to each of low-path filters 601a and 601b in addition to the high-path filters 604a and 604b constituting the digital processing part 52 and the low-path filters 601a and 601b produce direct current components and low frequency components corresponding to scattered light amount (haze) from minute roughness in the illumination spot 20 on the wafer. In this manner, outputs from the low-path filters 601a and 601b are supplied to a haze processing part 606 and subjected to processing of haze information. That is, the haze processing part 605 produces a signal corresponding to magnitude of haze in each place on the wafer from magnitude of input signals supplied from the low-path filters 601a and 601b as haze signal. Further, since angular distribution of the scattered light amount from the roughness is changed in accordance with spatial frequency distribution of the minute roughness, haze signals from the detectors of the plural detection parts 102 disposed in directions and angles different from one another are supplied to the haze processing part 606 as shown in FIGS. 13 to 23, so that information concerning the spatial frequency distribution of the minute roughness can be obtained from the haze processing part 606 on the basis of the intensity ratio thereof.

A modification example of the illumination intensity distribution formed on the sample surface by the illumination part 101 is described. The illumination intensity distribution having the Gaussian distribution in the longitudinal direction can be also used instead of the illumination intensity distribution extended in one direction and having the substantially uniform intensity in the longitudinal direction. The Gaussian distribution illumination extended in one direction is formed by the structure in which a spherical lens is included in the illumination intensity distribution control part 7 and an elliptical beam extended in one direction is formed by the beam expander 5 or by the structure in which the illumination intensity distribution control part 7 is composed of plural lenses containing cylindrical lenses. Part or all of cylindrical lenses or spherical lens included in the illumination intensity distribution control part 7 can be installed in parallel to the sample surface to thereby form the illumination intensity distribution extended in one direction on the sample surface and having the width which is narrow in the perpendicular direction to the extended direction. Variation of the illumination intensity distribution on the sample surface due to variation of the state of light incident on the illumination intensity distribution control part 7 is smaller and the stability of the illumination intensity distribution is higher as compared with the case where the uniform illumination intensity distribution is formed and further the transmission factor of light is high and the efficiency is satisfactory as compared with the case where a diffraction optical element, a micro lens array or the like is used in the illumination intensity distribution control part 7.

Figure 22:
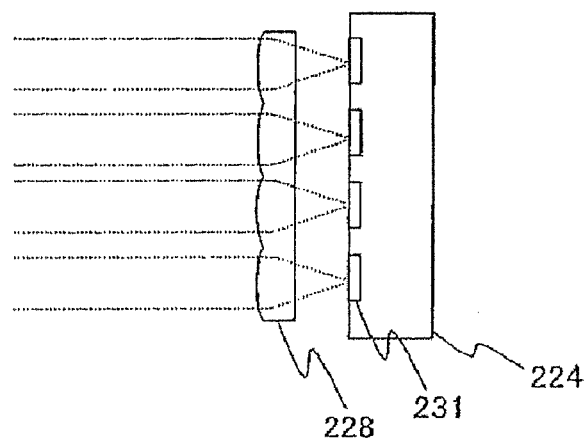
FIG. 22 is a diagram showing a second example of an array sensor according to the present invention.

FIG. 22 schematically illustrates a modification example of the array sensor 224. In the array sensor 224 having the arranged APD pixels, when individual APD pixels are small, the insensible area between the APD pixels is relatively larger than the effective area of the light receiving part of the APD pixels and accordingly there is a problem that the fill factor of the array sensor 224 is reduced and the light detection efficiency is reduced. Hence, a micro lens array 228 is disposed before the light receiving plane of the array sensor 224, so that the ratio of light incident on the insensible area between pixels can be reduced to thereby improve the effective fill factor. The micro lens array 228 includes minute convex lenses arranged at the same intervals as the arrangement intervals of the APD pixels and is disposed so that parallel light beams (shown by broken lines in FIG. 22) to the main optical axis of the incident light on the array sensor 224 enter the vicinity of the center of relevant APD pixels.

Figure 23:
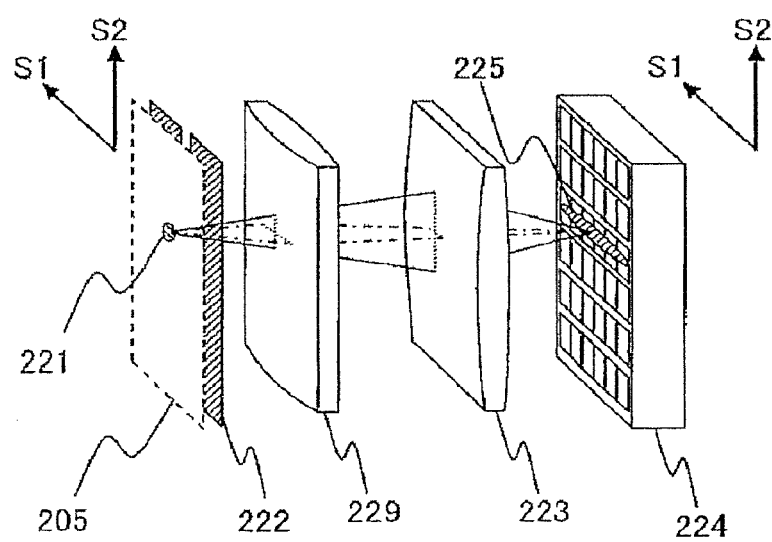
FIG. 23 is a diagram showing a second example of plural-pixel sensor of a detection part according to the present invention.

FIG. 23 schematically illustrates a modification example of the plural-pixel sensor 204. The plural-pixel sensor 204 includes one-axis focusing system 229 having the function of focusing in the S1 direction and one-axis focusing system 223 having the function of focusing in the S2 direction. The focusing magnification in the S1 direction is made higher than that in the S2 direction, so that the defect image 221 is enlarged in the S1 direction. When cylindrical lenses are used as the one-axis focusing systems 229 and 223, the one-axis focusing system 229 is disposed nearer to the conjugate plane 205 to the sample surface than the one-axis focusing system 223 to form the focusing relation in the S1 direction, so that the magnification in the S1 direction is higher than that in the S2 direction. In the structure (FIG. 18) described above, the optical intensity distribution in the S1 direction of the one-axis enlarged image 225 or magnitude of spread of the image is sometimes changed depending on angular distribution in the S1 direction of the scattered light on the conjugate plane 205 to the sample surface. In contrast, in the embodiment, the magnitude of the one-axis enlarged image 225 is decided by magnitude of the defect image 221 and the focusing magnification in the S1 and S2 directions decided by the structure and arrangement of the one-axis focusing systems 229 and 223. Since the magnitude of the defect image 221 of the minute defect is decided by the optical resolution degree of the detection part 102 as described above, change of the magnitude of the one-axis enlarged image 225 is small and stable inspection result is obtained.

A photomultiplier having high electron multiplication factor ($10^4$ or more) may be used instead of the avalanche photodiodes which are constituent elements of the array sensor 224. Since the size of individual pixels can be made small when the avalanche photodiodes are used, there are merits that the optical magnification of the detection part 102 can be reduced and integration exceeding several hundred pixels and several thousand pixels can be made at low cost. In contrast, there is a merit that the photomultiplier has low temperature dependence of the electron multiplication factor and is stable.

Further, the present invention is not limited to the above embodiments and various modification examples are contained. For example, the above embodiments have been described in detail for easy understanding of the present invention and are not necessarily limited to provision of all the structure described. Moreover, part of the structure of an embodiment may be replaced by the structure of another embodiment and further the structure of an embodiment may be added to the structure of another embodiment. Further, part of the structure of the embodiments may be subjected to addition, deletion and replacement of other structure.

REFERENCE SIGNS LIST

2 . . . light source
5 . . . beam expander
6 . . . polarization control part
7 . . . illumination intensity distribution control part
24 . . . illumination intensity distribution monitor
53 . . . control part
54 . . . display part
55 . . . input part
101 . . . illumination part
102 . . . detection part
103 . . . stage
105 . . . signal processing part
201 . . . objective lens
202 . . . polarizing filter
203 . . . focusing lens
204 . . . plural-pixel sensor
224 . . . array sensor

The invention claimed is:

1. A defect inspection method comprising:
an illumination light adjustment step of adjusting light emitted from a light source to light flux having desired light amount, position, beam diameter and polarization state;
an illumination intensity distribution control step of leading the light flux obtained in the illumination light adjustment step to a surface of a sample with a desired incident angle and forming illumination intensity distribution which is long in one direction and short in a direction perpendicular to the one direction on the surface of the sample;
a sample scanning step of displacing the sample in a direction substantially perpendicular to a longitudinal direction of the illumination intensity distribution in an illumination light irradiation position on the surface of the sample by the illumination intensity distribution control step;

a scattered light detection step of extending scattered light, emitted from an area on the surface irradiated with illumination light in the illumination intensity distribution control step, in the sample scanning step over a plurality of avalanche photodiode pixels using a detection lens group including a minute convex lens array and outputting scattered light detection signals corresponding to a total number of photons incident on each of the avalanche photodiode pixels;

a defect judgment step of processing the plurality of scattered light detection signals obtained in the scattered light detection step to judge presence of a defect; and a display step of displaying position on the surface of the sample for each place in which the defect is judged to be present in the defect judgment step.

* * * * *